United States Patent
Sullivan et al.

(10) Patent No.: US 9,909,962 B2
(45) Date of Patent: Mar. 6, 2018

(54) DEVICE AND METHOD FOR CONTROLLING THE TEMPERATURE IN A MOVING FLUID IN A LABORATORY SAMPLE PROCESSING SYSTEM

(71) Applicant: STATSPIN, INC., Westwood, MA (US)

(72) Inventors: Kevin J. Sullivan, Chestnut Hill, MA (US); James Kelland, East Walpole, MA (US); Nhat Khai L. Nguyen, Boston, MA (US)

(73) Assignee: LEICA BIOSYSTEMS RICHMOND, INC., Richmond, IL (US)

(*) Notice: Subject to any disclaimer, the term of this patent is extended or adjusted under 35 U.S.C. 154(b) by 713 days.

(21) Appl. No.: 14/382,944

(22) PCT Filed: Mar. 8, 2013

(86) PCT No.: PCT/US2013/029747
§ 371 (c)(1),
(2) Date: Sep. 4, 2014

(87) PCT Pub. No.: WO2013/134583
PCT Pub. Date: Sep. 12, 2013

(65) Prior Publication Data
US 2015/0044664 A1      Feb. 12, 2015

Related U.S. Application Data

(60) Provisional application No. 61/608,762, filed on Mar. 9, 2012.

(51) Int. Cl.
*G01K 1/14*     (2006.01)
*G01N 1/31*     (2006.01)
(Continued)

(52) U.S. Cl.
CPC .......... *G01N 1/312* (2013.01); *B01F 11/0017* (2013.01); *B01F 15/00175* (2013.01);
(Continued)

(58) Field of Classification Search
CPC combination set(s) only.
See application file for complete search history.

(56) References Cited

U.S. PATENT DOCUMENTS 5,061,630 A    10/1991   Knopf et al.
5,104,621 A     4/1992   Pfost et al.
(Continued)

FOREIGN PATENT DOCUMENTS

EP    0434592 A1    6/1991
JP    2004-294130 A1 * 10/2004  ............. G01N 35/00
(Continued)

OTHER PUBLICATIONS

Steven Q. Irvine, "Whole-mount in situ hybridization of small invertebrate embryos using laboratory mini-columns," Bio Techniques, vol. 43(6):764-768 (2007).

*Primary Examiner* — Lisa Caputo
*Assistant Examiner* — Nasir U Ahmed
(74) *Attorney, Agent, or Firm* — Preti Flaherty Beliveau & Pachios LLP (57) ABSTRACT

A temperature control device and method are provided for an analytical system for performing laboratory protocols. The device includes a well within a housing configured to receive a biological specimen according to a predetermined sample process. The specimen is suspended by a holding device in the well. A thermal element is provided in heat exchange communication with fluid in the well. A temperature sensor is located in the well at a location to be covered and uncovered by rocking motion of fluid in the well. A controller, in communication with the thermal element, the (Continued)

temperature sensor, and an agitation system, is operative to control the thermal element in correlation with temperature data, for example, peak temperature data, from the temperature sensor.

25 Claims, 8 Drawing Sheets

(51) Int. Cl.
  *G01N 35/00* (2006.01)
  *G05D 23/19* (2006.01)
  *B01F 11/00* (2006.01)
  *B01F 15/00* (2006.01)

(52) U.S. Cl.
  CPC . *B01F 15/00396* (2013.01); *G01N 35/00029* (2013.01); *G05D 23/19* (2013.01); *G01N 2035/00138* (2013.01); *G01N 2035/00396* (2013.01); *G01N 2035/00524* (2013.01); *Y10T 436/112499* (2015.01); *Y10T 436/115831* (2015.01)

(56) References Cited

U.S. PATENT DOCUMENTS

| | | | |
|---|---|---|---|
| 5,167,615 A | 12/1992 | East et al. | |
| 5,437,838 A | 8/1995 | DeMoranville et al. | |
| 5,443,791 A | 8/1995 | Cathcart et al. | |
| 5,625,706 A | 4/1997 | Lee et al. | |
| 5,637,208 A | 6/1997 | Dourdeville | |
| 5,674,006 A | 10/1997 | Islam et al. | |
| 5,695,720 A | 12/1997 | Wade et al. | |
| 5,897,781 A | 4/1999 | Dourdeville | |
| 5,993,654 A | 11/1999 | Black | |
| 6,180,061 B1 | 1/2001 | Bogen et al. | |
| 6,212,705 B1 | 4/2001 | Kramer | |
| 6,235,479 B1 | 5/2001 | Rogers | |
| 6,238,910 B1 | 5/2001 | Custance et al. | |
| 6,296,809 B1 | 10/2001 | Richards et al. | |
| 6,432,696 B2 | 8/2002 | Custance et al. | |
| 6,485,913 B1 | 11/2002 | Becker et al. | |
| 6,607,907 B2 | 8/2003 | McNeely et al. | |
| 6,615,856 B2 | 9/2003 | McNeely et al. | |
| 6,637,463 B1 | 10/2003 | Lei et al. | |
| 6,663,353 B2 | 12/2003 | Lipscomb et al. | |
| 6,793,890 B2 | 9/2004 | Morales et al. | |
| 6,827,901 B2 | 12/2004 | Copeland et al. | |
| 6,881,579 B2 | 4/2005 | Hilson et al. | |
| 7,013,978 B2 | 3/2006 | Appleford et al. | |
| 7,056,477 B1 | 6/2006 | Schwalbe et al. | |
| 7,223,363 B2 | 5/2007 | McNeely et al. | |
| 7,235,400 B2 | 6/2007 | Adey | |
| 7,358,078 B2 | 4/2008 | Chen et al. | |
| 7,390,458 B2 | 6/2008 | Burow et al. | |
| 7,468,161 B2 | 12/2008 | Reinhardt et al. | |
| 7,557,070 B2 | 7/2009 | Ravkin et al. | |
| 7,612,020 B2 | 11/2009 | Stuelpnagel et al. | |
| 7,614,857 B2 | 11/2009 | Fuechslin et al. | |
| 7,964,413 B2 * | 6/2011 | Macioszek | C12Q 1/6813 422/52 |
| 7,985,375 B2 | 7/2011 | Edens et al. | |
| 8,501,115 B2 | 8/2013 | Adey et al. | |
| 2001/0046700 A1 | 11/2001 | Custance | |
| 2005/0005780 A1* | 1/2005 | Beretta | A47J 31/4489 99/453 |
| 2005/0239195 A1* | 10/2005 | Oram | G02B 21/34 435/288.3 |
| 2006/0088451 A1 | 4/2006 | Nakamima et al. | |
| 2006/0141635 A1 | 6/2006 | Taneike | |
| 2008/0014576 A1 | 1/2008 | Jovanovich et al. | |
| 2008/0247914 A1 | 10/2008 | Edens et al. | |
| 2009/0008405 A1 | 1/2009 | Mathus et al. | |
| 2009/0170714 A1* | 7/2009 | Shimamoto | B01F 11/0017 506/7 |
| 2009/0275113 A1* | 11/2009 | Maltezos | B01L 3/50851 435/286.1 |
| 2009/0305337 A1 | 12/2009 | Iqbal et al. | |
| 2010/0009335 A1* | 1/2010 | Joseph | C12M 23/12 435/3 |
| 2010/0113288 A1 | 5/2010 | Adey et al. | |
| 2010/0167943 A1 | 7/2010 | Adey et al. | |
| 2010/0200021 A1 | 8/2010 | Adey et al. | |
| 2010/0291536 A1 | 11/2010 | Viljoen et al. | |
| 2011/0232769 A1* | 9/2011 | Nichogi | G01N 35/025 137/3 |

FOREIGN PATENT DOCUMENTS

| | | |
|---|---|---|
| JP | 2011-007496 A | 1/2011 |
| WO | WO 95/05590 A1 | 3/1995 |
| WO | WO 2009/034783 A1 | 3/2009 |
| WO | WO 2010/048631 A2 | 4/2010 |
| WO | WO 2010/132756 A2 | 11/2010 |
| WO | WO 2011/139888 | 11/2011 |

* cited by examiner

DEVICE AND METHOD FOR CONTROLLING THE TEMPERATURE IN A MOVING FLUID IN A LABORATORY SAMPLE PROCESSING SYSTEM

STATEMENT REGARDING FEDERALLY SPONSORED RESEARCH OR DEVELOPMENT

N/A

BACKGROUND OF THE INVENTION

A large number of analytical methods and tools exist today in the scientific work place that can be used for testing samples of a wide variety. Some laboratory protocol systems use fluid baths with heating and/or cooling capabilities to precisely control the temperature of chemical and biochemical reactions. For example, it is known to circulate a heat transfer fluid in a bath over an object, resulting in heat transfer between a heating and cooling element and the object via the fluid. In some systems, the fluid also reacts directly with the object. For example, in the particular case of biological specimens mounted on glass microscope slides, the slides are immersed in a fluid that is both a reagent that performs a sample treatment function and a heat transfer agent.

Exemplary laboratory systems are shown in WO 2011/139888, entitled "Analytical System for Performing Laboratory Protocols and Associated Methods," and US Patent Publication No. 2010-0113288, entitled "Modular System for Performing Laboratory Protocols and Associated Methods."

SUMMARY OF THE INVENTION

A temperature control device and method are provided for an analytical system for performing laboratory protocols on objects such as biological specimens immersed in a fluid. The temperature of a biological specimen can be precisely controlled by correlation with temperature measurements in the moving fluid at a location remote from the specimen.

In one embodiment, the device includes a well within a housing configured to receive a biological specimen according to a predetermined sample process. A thermal element is provided in heat exchange communication with a heat transfer fluid in the well. A temperature sensor is located in the well at a location to be covered and uncovered by rocking motion of fluid in the well. The device includes an agitation system to move the housing, thereby causing motion of the fluid with respect to the housing. The specimen is suspended in a pivotable holding device in the housing for motion with respect to the housing and to remain in substantial contact with the fluid. A controller, in communication with the thermal element, the temperature sensor, and the agitation system, is operative to control the thermal element in correlation with temperature data, for example, peak temperature data, from the temperature sensor as it is covered and uncovered by the fluid.

DESCRIPTION OF THE DRAWINGS

The invention will be more fully understood from the following detailed description taken in conjunction with the accompanying drawings in which.

DETAILED DESCRIPTION OF THE INVENTION

Laboratory protocol systems use fluid baths with heating and/or cooling capabilities to precisely control the temperature of chemical and biochemical reactions. Typically, a heat transfer fluid in the bath is circulated by a pump that produces high velocity turbulent flow, resulting in efficient heat transfer from a heating and cooling element to the object to be heated or cooled. In some systems, the object is exposed to the fluid and the fluid reacts directly with the object. For example, in the particular case of biological specimens mounted on glass microscope slides, the fluid in which the slides are immersed is often a reagent that performs a sample treatment function as well as being a heat transfer agent.

The present invention relates to an analytical system for performing laboratory protocols that provides precise control of the temperature in a moving fluid exposed to an object, such as a biological specimen mounted on a slide. Biological specimens are often fragile and can be damaged if exposed to turbulent flow. Gentle mixing of the reagent can be achieved by rocking the container housing the specimen, but the laminar flow results in larger temperature gradients between the heating surface and the heated object than in the case of turbulent mixing. Precise control of the reaction temperature can ideally be achieved by measuring the temperature at the reaction site; however, this is typically not practical.

In the present invention, a temperature sensor is located in contact with the reagent bulk fluid, and a thermal element is controlled in correlation with measured temperature fluctuations as the fluid moves past the sensor. By properly locating the temperature sensor in the fluid flow path and synchronizing the sensor temperature measurement with the rocking movement of the fluid, temperature sensing errors can be reduced. In one example, the system and method can achieve temperature control within ±1° C. The system and method can also accommodate rapid, controlled changes in temperature which may be required by a particular process, while minimizing the volume of heat transfer fluid. Reducing fluid volumes reduces the cost of consumed reagents.

Figure 1:
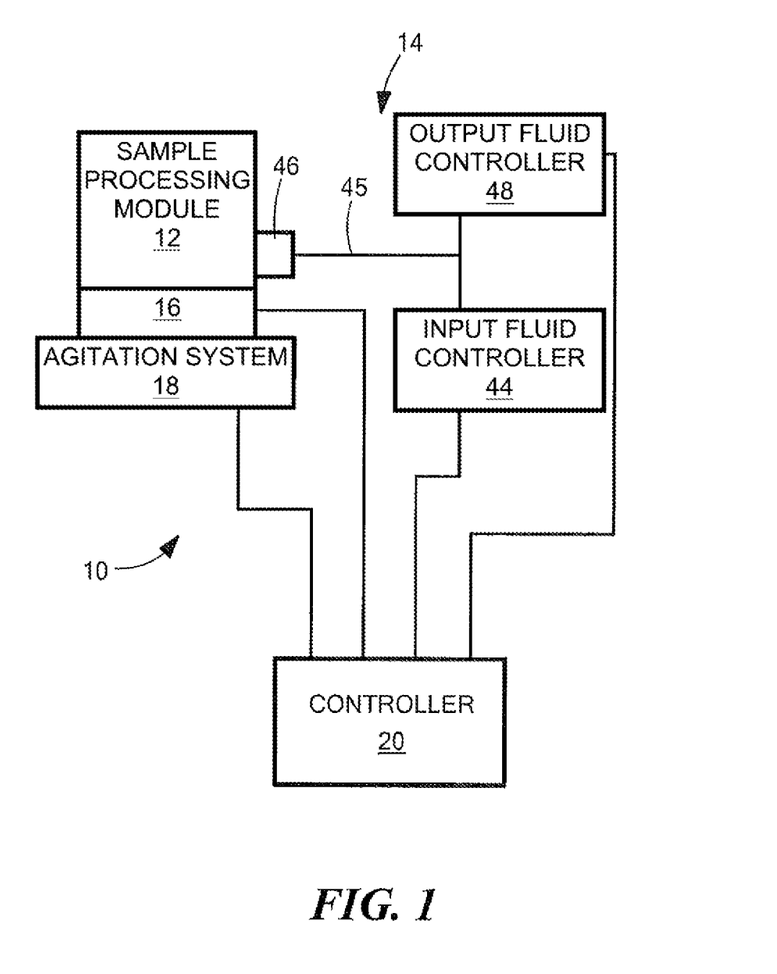
FIG. 1 is a schematic illustration of an embodiment of an analytical system for performing laboratory protocols in accordance with the present invention.
Figure 2:
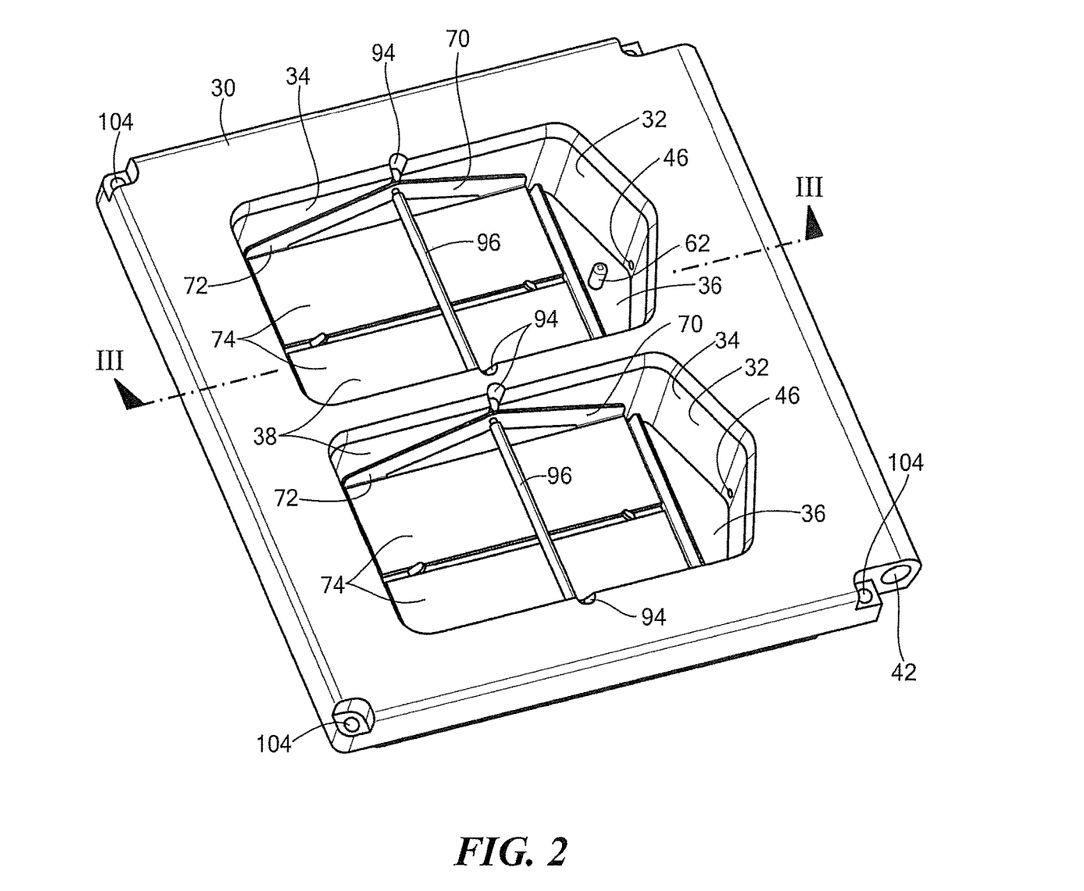
FIG. 2 is an isometric view of a sample processing module with a housing and a device for holding slides containing biological specimens.
Figure 3:
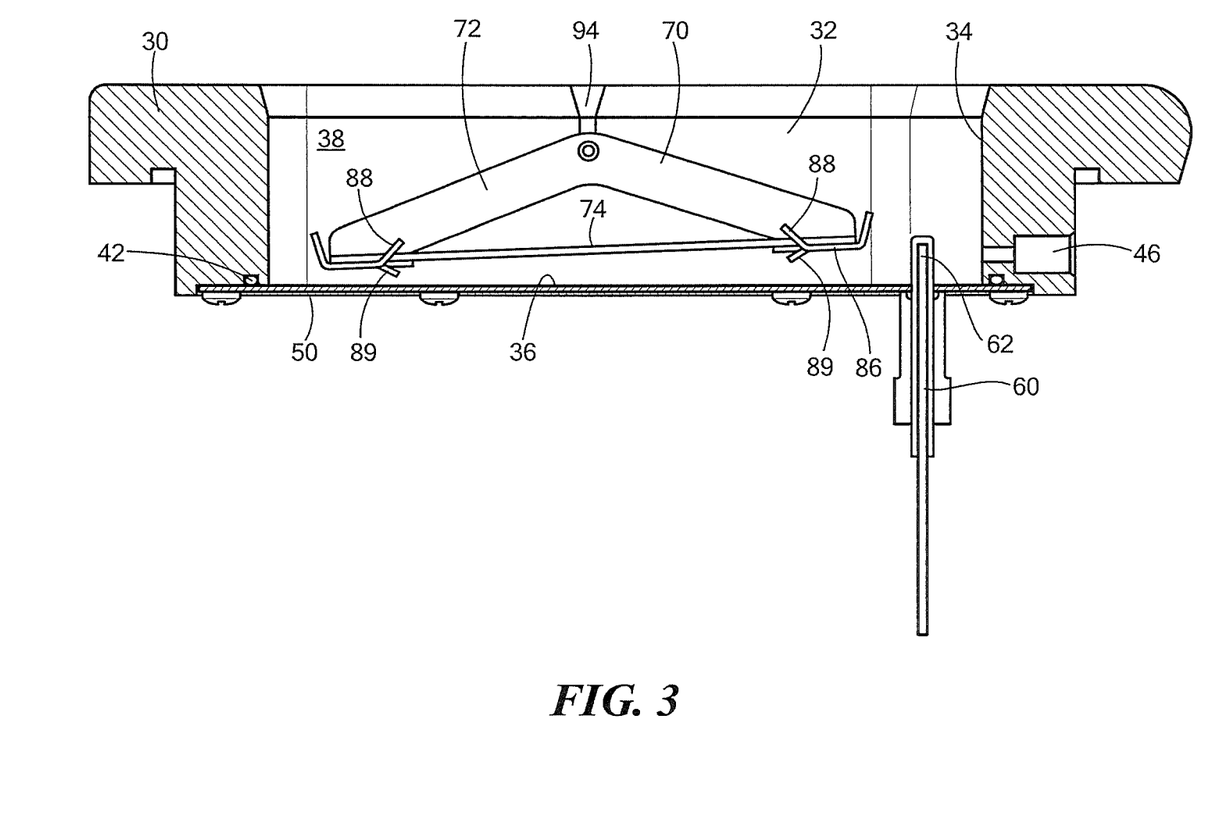
FIG. 3 is a cross-sectional view taken along line III-III of FIG. 2.
Figure 4:
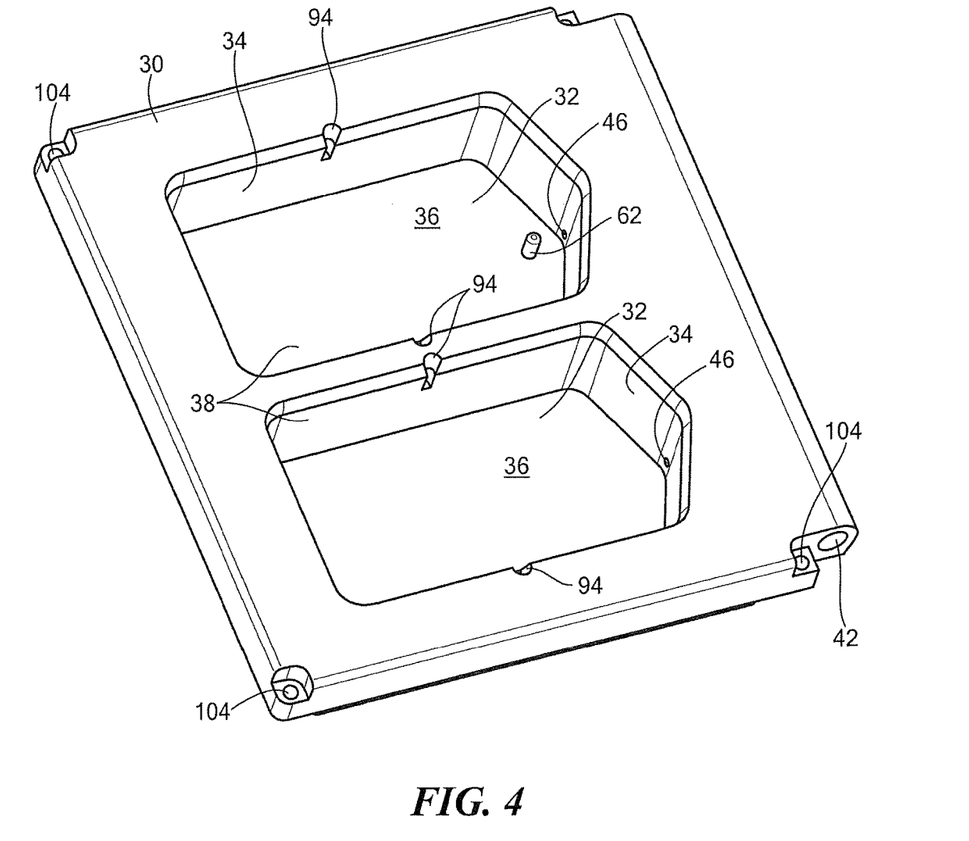
FIG. 4 is an isometric view of the housing of the module of FIG. 2.
Figure 5:
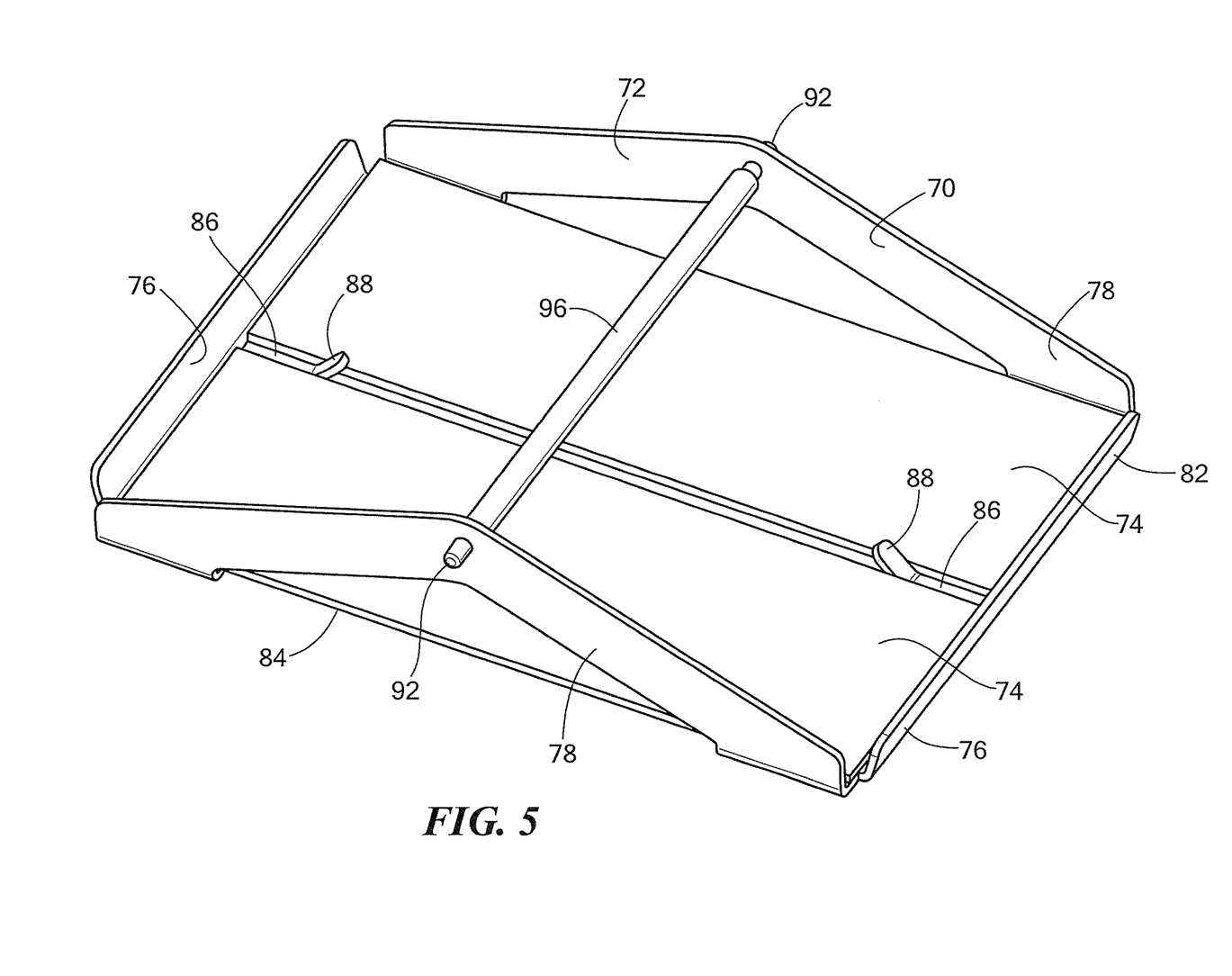
FIG. 5 is an isometric view of the device for holding slides of FIG. 2.

An exemplary analytical system for performing laboratory protocols is illustrated schematically in FIG. 1. The system 10 incorporates at least one sample processing module 12 to process a laboratory protocol on a biological specimen. The system includes a fluidics system 14 for the input and output of fluids, a temperature control system 16, and an agitation system 18. The temperature control system of the sample processing module is configured to regulate the temperature of the sample process. The agitation system is configured to provide agitation of the sample processing module to move the reagent/heat transfer fluid past the specimen. The system also includes a system controller 20 that interfaces with the fluidics system 14, the temperature control system 16, and the agitation system 18.

One embodiment of a sample processing module 12 for use with the analytical system is shown in FIGS. 2-5. The sample processing module includes a housing 30 configured to accommodate one or more sample holding devices 70. The housing includes one or more wells 32 formed by upstanding walls 34 and a floor 36. Each well defines an internal space or chamber 38 to accommodate a sample holding device. Two wells for accommodating two sample holding devices are illustrated is FIGS. 2 and 4, although one or any other number of wells can be provided within the housing. The internal space in each well allows the introduction and retention of fluids around a sample for the performance of a laboratory protocol. Thus, fluid reagents, fluid washes, buffers, and the like can be contained within the well during heating, cooling, agitation, or any other protocol step. A cover 40 can be attached to the housing 30 to cover the well during the process. In one configuration, the cover can be hingedly attached at hinge points 42 to allow the well to be covered and uncovered while minimizing risk of misplacing the cover.

The temperature control system 16 includes a thermal element 50 in heat transfer relationship with one or more surfaces of the housing for heat exchange with a fluid in the well. (See FIG. 3.) In one configuration, the floor 36 of the housing is a suitable surface for heat transfer between the thermal element and a fluid within the wells, and the thermal element is thermally coupled to the floor. In one configuration, the housing floor can be formed by a plate attached to the upstanding walls, for example, with screws or other fastener elements. A sealing element 42 is provided between the plate and the walls to fluidically seal the chamber. Alternatively, the floor can be formed integrally with the walls of the housing. The floor can be formed of any suitable material for transferring heat. Various metals, such as aluminum, copper, or any other thermally conductive metal, including alloys, can be used. Alternatively, thermally conductive non-metals can be used, such as diamond-like carbon, graphite, and the like.

The temperature control system also includes a temperature sensor 60 within the well and in communication with the system controller. The temperature sensor can be any suitable temperature sensor, such as a thermistor, a resistance temperature device, thermocouple, or the like. In one configuration, the temperature sensor is in the form of a probe 62 that extends through a sealed aperture in the housing floor 36 at one end of the chamber. The system controller 20 controls the thermal element 50 in correlation with temperature measurements received from the sensor 60, described further below. In one exemplary embodiment, the sensor can be capable of providing a temperature measurement within a time span of one second. The sensor can be operative over a temperature range of 0° C. to 100° C. and have a precision of ±0.1° C. Suitable commercially available sensors include platinum resistance sensor #F1540-100-1/10B or thermistor element #44031 commercially available from Omega Engineering.

In one embodiment, the thermal element 50 includes one or more Peltier elements thermally coupled to a heat transfer surface of the housing 30, such as the housing floor 36. Electrical current delivered to a Peltier device causes one side of the device to heat and the other side to cool. Reversing the polarity of the current causes a reversal in which side is heated and which side is cooled. Thus, the system controller provides electrical input to the Peltier elements to regulate heating or cooling of the sample processing module. By coupling such devices to the housing, the sample processing module temperature can be controlled. Such control can include maintaining a given temperature during a reaction, providing heating or cooling to the reaction, cycling the temperature during the reaction, and the like. Fans can be associated with the Peltier elements to dissipate heat or cold from the side of the Peltier device that is not controlling the temperature of the reaction. For example, if the sample processing module is being cooled, the opposite side of the Peltier device becomes hot, and thus the fans function to cool the hot side. Thermal fins can also be associated with the Peltier device to assist in this thermal regulation.

Various other configurations for the thermal element 50 are contemplated, and any device capable of regulating the temperature of the sample process can be considered to be within the present scope. For example, the thermal element can be a thermally conductive material associated with the housing in a position that allows thermal regulation to occur. The material of the thermal element can be any thermally conductive material, such as, for example, materials that can be used in common heat spreaders. Various metals can be used, such as aluminum, copper, or any other thermally conductive metal, including associated alloys. Additionally, thermally conductive non-metals can also be utilized. Non-limiting examples include diamond-like carbon, graphite materials, and the like. Further non-limiting examples of thermal elements include etched foil heaters, wirewound heaters, thick film heaters, and thin film heaters.

The housing 30 of the sample processing module can be made from a variety of materials. The interface between the sample process and the housing should be substantially inert with respect to the sample process. As such, the housing material itself can be substantially inert, or a coating can be applied to any surfaces of the housing or chamber that will come in contact with the materials of the sample process. Generally, however, the housing can be made from metals, such as aluminum, copper, stainless steel, nickel, and alloys thereof, from polymeric materials, ceramics, and the like. Coatings for protective purposes can include modified surfaces such as anodized layers on an aluminum surface, or polymeric or other inert coatings that can provide adequate protection between the housing material and the sample process. The cover 40 can be formed of a transparent material or can include a transparent window to allow visual access to the sample process.

The fluidics system 14 includes an input fluid controller 44 in communication with a fluid port 46 and configured to deliver fluid via a fluid line 45 to the sample processing module 12. (See FIG. 1.) The fluid can be withdrawn from a fluid reservoir by the input fluid controller 44. The fluidics system can additionally include an output fluid controller 48 in communication with the fluid port 46. The output fluid controller is configured to remove fluid from the sample processing module via the fluid line 45, which is bidirectional along at least one section in this configuration. The output fluid controller can deliver the output fluid to an output fluid container, such as a waste container. Various other system configurations are contemplated within the scope of the present invention. For example, the input fluid controller and output fluid controller can employ separate fluid lines and separate input and output ports. In another example, the input fluid controller can deliver fluids from multiple fluid reservoirs, using, for example, an input fluid distribution valve. Similarly, the output fluid controller can withdraw fluid from the sample processing module and deliver that fluid to multiple output fluid containers, using, for example, an output fluid distribution valve.

A fluid port 46 is provided for each well 32 capable of interfacing with the input fluid controller 44 and the output fluid controller 48. (See FIGS. 2-4.) The fluid port 46 is configured to allow fluid to enter the chamber 38 of the sample processing module under control of the input fluid controller 44 and exit the chamber under control of the output fluid controller 48. In one configuration, the fluid port 46 is a passageway through a wall 34 of the housing 30 configured to receive a fitting, coupling, tubing, channel, pipe, or other fluidic structure. (See, for example, FIG. 3.) The input and output fluid controllers can be coupled to the port directly or via, for example, fluidic tubing. In one specific configuration, the fluid port is configured to receive an end of fluidic tubing. The input fluid controller can include a pump system fluidically coupled to the fluidic tubing. Similarly, the output fluid controller can include a pump system fluidically coupled to the fluidic tubing, or any other system that provides a vacuum force to the fluidic tubing. In some cases, gravity or capillary forces can be used in lieu of a pump to draw fluid from the chamber. In another aspect, the fluid port can be an open portion of the well of the sample module, and the input fluid controller and the output fluid controller can each be a pipette (not shown).

The fluidics system 14 can include any and all components that are necessary to move fluid into and out of the sample processing module. A variety of pumping mechanisms can be utilized to perform the various pumping functions of the present invention. Non-limiting examples of such pumping mechanisms can include peristaltic pumps, syringe pumps, screw pumps, piston pumps, and the like. In another aspect, the transfer of fluid can be discontinuous, as would be the case for systems where the fluid port is an open portion of the well and the fluid controllers are a pipette or other discontinuous fluid transfer device. Such a discontinuous fluid transfer system can be facilitated by utilizing a robotic arm attachment in conjunction with the fluidics system. A manifold device can be provided to control the distribution of the fluids in the system. The manifold device can incorporate any of a variety of fluid handling components, such as couplings, channels, fittings, valves, pumps, filters, and the like. A manifold device can provide advantages such as reducing dead volume, reducing part count, providing higher reliability, and improving manufacturability. Other fluid components and functions can be conveniently incorporated into a manifold device, such as flow meters, flow indicators, sensors, such as pH sensors, and the like.

The sample processing module 12 includes a sample holding device 70 to support a biological specimen for reaction with a reagent in a pre-determined sample process. In one embodiment, the support device is a slide holder 72 configured to hold one or more microscope slides 74, each containing a biological specimen. The slide holder fits within the well 32 in the housing 30. In the embodiment shown, each slide holder holds two slides, although the slide holder can be configured to hold any number of slides. In one configuration, the slide holder includes two end members 76 and two side members 78 forming a frame 82 and defining a substantially open bottom region 84. (See FIG. 5.) The end members include a lip 86 on which ends of each slide can rest. The lips may include one or more upstanding tabs 88 to keep adjacent slides spaced apart and to hold the slides in place without movement with respect to the frame. Downwardly facing tabs 89 prevent the slide from contacting any surface on which they may be placed during handling or otherwise. Typically, the slide is placed in the slide holder with the biological specimen on the slide facing downwardly toward the floor 36 of the housing, accessible through the open bottom region 84 of the slide holder 72. In this manner, a minimal volume of fluid can be delivered into the well for contact with the biological specimen.

The slide holder 72 can be configured to be mounted within the housing 30 for rocking movement with respect to the housing. In one configuration, pivot pins 92 extend outwardly at a midpoint of the slide holder from each side member 78 and fit within recesses 94 in opposed side walls 34 of the housing 30. In this manner, the slide holder can rock about an axis defined through the pivot pins when the housing 30 is agitated by the agitation system 18. A handle element 96 can extend across the top of the slide holder to aid in placing the slide holder in and lifting the slide holder out of the housing. Placing and lifting of the slide holder can be automated, for example, via a robotic arm attachment, or manual.

Figure 6:
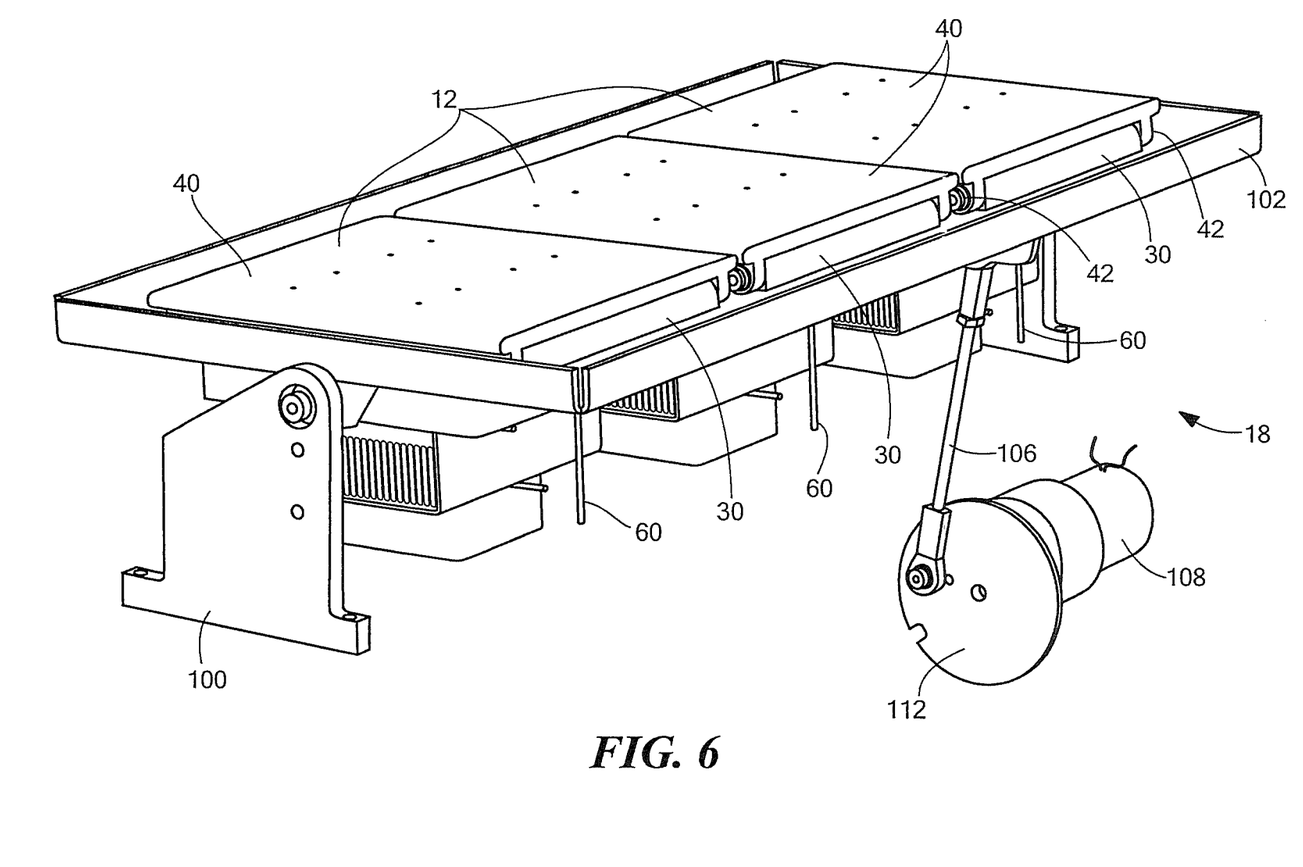
FIG. 6 is a perspective view of an agitation system of an analytical system with several sample processing modules.

One embodiment of an agitation system 18 is shown in FIG. 6. The system includes a support structure 100, including, for example, a rocker table 102, to which one or more sample processing modules 12 are mounted, for example, with screws or other fastener devices (not shown) through apertures 104 in the housing 30. Other non-limiting examples for mounting the housing to the rocker table can include clips, adhesive materials, and magnetic devices. A linkage assembly 106 driven by a suitable motor 108 or other motion generating device is attached to the rocker table. One end of the linkage assembly is attached to a rotatable plate 112 for circular, eccentric, or other motion about the axis of a motor shaft. Another end of the linkage assembly is fixed to the rocker table 102. In this manner the rocker table can be driven with a back and forth rocking motion. The linkage assembly can be adjustable to vary the travel of the rocker table and thus provide a variety of repetitive motions to the sample processing module. Such motions can include vibration, back and forth motion, circular motion, rocking motion, tilting motion, and the like.

The agitation system 18 can be configured to provide a constant back and forth travel, or it can be configured to provide a variable travel. For example, the rocker table can be rocked with a steeper slope on the forward motion and a lesser slope on the backward motion. Additionally, the rocker table can be maintained in an angled position to facilitate the removal of fluids from the sample modules. The motor can be a variable speed motor, thus allowing changes in agitation frequency as well as amplitude. Additionally, positional sensors can allow the rocker table to be held horizontally to allow even fluid coverage of the samples, or held in an angled position to allow draining.

The agitation system 18 can function in conjunction with the fluidics system 14 under control of the system controller 20 to facilitate delivery and removal of fluid to and from the sample processing module(s) 12. For example, a module can be filled with fluid and rocked back and forth to provide agitation to the sample process. To add a fluid, the agitation system can move and hold the rocker table in a substantially horizontal position such that fluid can be dispensed evenly into the chamber. In another aspect, the agitation system may tilt and hold the rocker table downwardly in the direction of the fluid input while fluid is added. Such motion may be desirable for an analysis where the fluid is to contact all portions of the sample on the slide substantially simultaneously, or for the purposes of eliminating bubbles in, or degassing, the fluid. To remove a fluid, the agitation system can move the rocker table to a tilted position such that fluid can accumulate at the fluid port in order to facilitate fluid removal. As an example, a sample processing module can be agitated at a slight rocking tilt, such as 10°, during a wash step. Once the wash is finished, the agitation system can tilt the sample processing module to a greater angle, such as 30°, in order to drain the fluid from the module. It should be noted that the angles described in association with agitation are intended to be merely exemplary. As such, various ranges of angles could be used in a similar manner to what is described.

In operation, a slide 74 is mounted with the specimen face down in the slide holder 82 and placed in the well 32 of the housing 30. The well is filled with a treatment fluid. To minimize the consumption of reagents, which can be expensive, the fill volume is limited by using only enough fluid to fully contact the bottom of the slide where the specimen is located. The required fill volume can be further reduced by configuring the slide holder and or the housing to minimize the fluid-filled gap between the slide and the floor. Because of heat losses to the local environment and the thermal mass of the walls and cover, there are often significant temperature gradients between the heating (or cooling) surface and the slide surface. These gradients can be reduced by mixing the fluid between the housing floor and slide surface with the agitation system, but they remain substantial. For example, in one typical situation with a well-mixed layer, maintaining a slide surface at 80° C. requires a floor temperature of 84° C. This offset makes it difficult to precisely control fluid temperature at the slide surface by measuring and regulating temperature at the heating or cooling surface.

The present method indirectly measures the temperature of the fluid at the slide surface by synchronizing the reading of the fluid temperature sensor 60 with the rocking motion used to mix the fluid. The slide 74 is suspended above the floor of the well and a thin layer of temperature controlled treatment fluid fills the gap between the slide and the floor 36. The treatment fluid is heated or cooled by the thermal element 50 coupled to the floor or walls, or otherwise thermally coupled to the treatment fluid. The heating and cooling output of the thermal element is regulated by controlling electronics of the system controller 20, which receive feedback of the treatment fluid temperature from the sensor 60 immersed in the treatment fluid.

Heat transfer between the chamber floor, the treatment fluid and the slide surface is enhanced by fluid flow which is generated by rocking the chamber in a see-saw fashion. The rocking generates a periodic wavelike flow as the bulk of the fluid alternately moves from one end of the tilted chamber to the other. The specimen on the slide surface remains substantially in contact with the fluid as the slide holder also rocks with respect to the housing. The temperature sensor is located in one end of the chamber, and is periodically immersed in the circulating fluid and then periodically exposed as the rocking motion moves the bulk of the fluid to the opposite end of the chamber. The temperature reported by the sensor 60 varies cyclically as the fluid flows over it and then retreats to the opposite end of the chamber in response to the rocking motion. We have found that the temperature reported by the sensor at the time it is immersed in the fluid that has just flowed from the gap between the slide and the chamber floor gives the best estimate of the average temperature at the slide surface, which is the process variable to be controlled. By synchronizing the temperature reading with the rocking motion, the best estimate of slide surface temperature can be extracted and used as feedback to the temperature control system.

EXAMPLE

Figure 7:
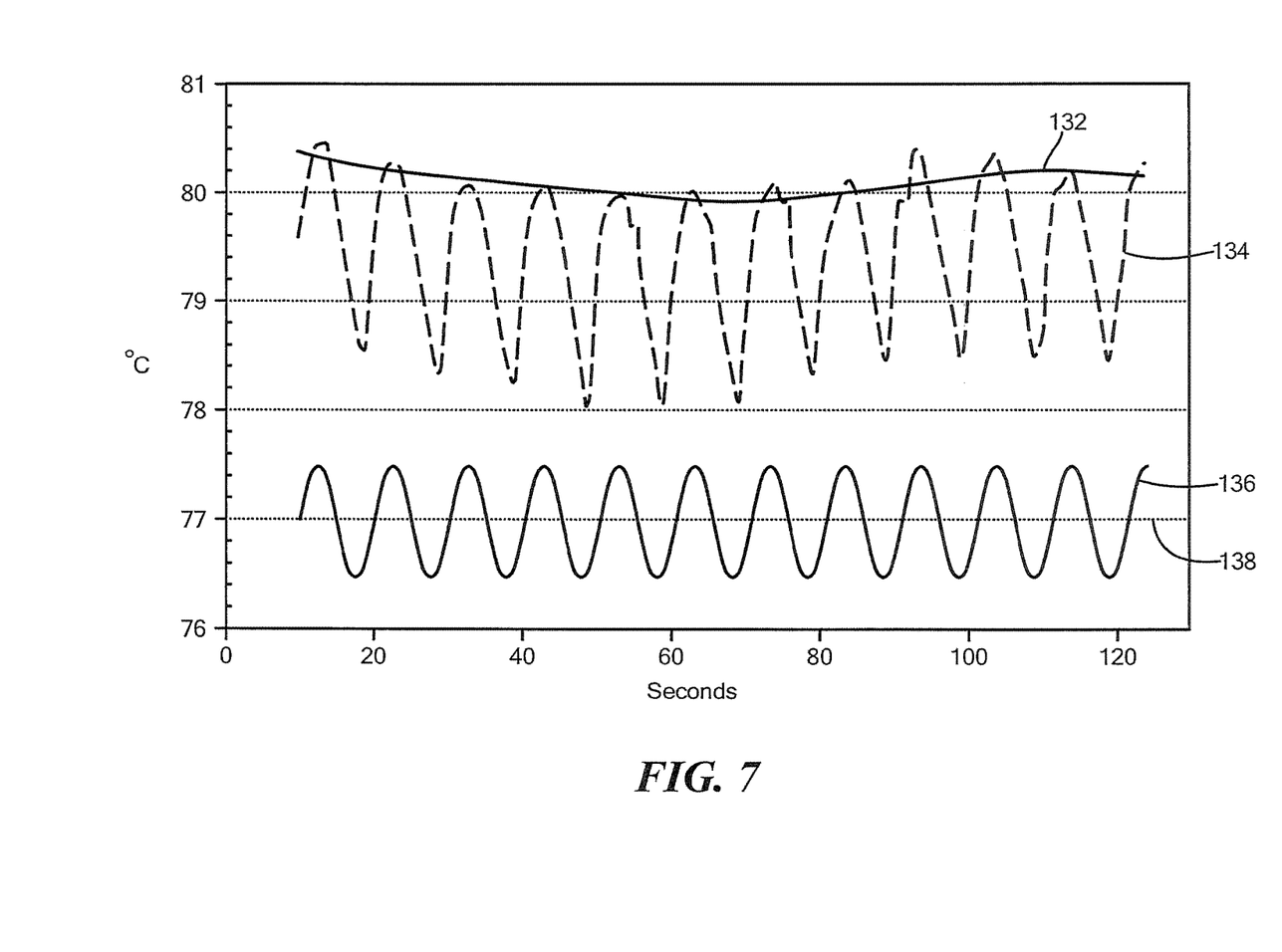
FIG. 7 is a graph illustrating an example of operation of a method according to the present invention.

To illustrate this method, FIG. 7 shows two minutes of operation with a controlled slide surface temperature of 80° C. The bold trace 132 is the actual temperature measured on the slide at the sample surface, as measured by a temperature sensor on the slide for experimental purposes. The dashed line 134 shows the temperature reported by the sensor 60 immersed in the moving fluid. The lower trace 136 represents the rocking motion of the sample chamber. In this example, the chamber is rocking at a rate of six cycles per minute. Each time the lower trace crosses the axis 138 the chamber is level. Each positive peak of the lower trace corresponds to the chamber being fully tilted with the fluid bulk located in the end of the chamber containing the sensor 60. The dashed line 134 shows that the sensor temperature peaks around the time it is fully immersed in the fluid that has just flowed from under the slide and that this peak temperature is closely correlated to the average temperature at the slide surface shown in the bold trace 132.

Figure 8:
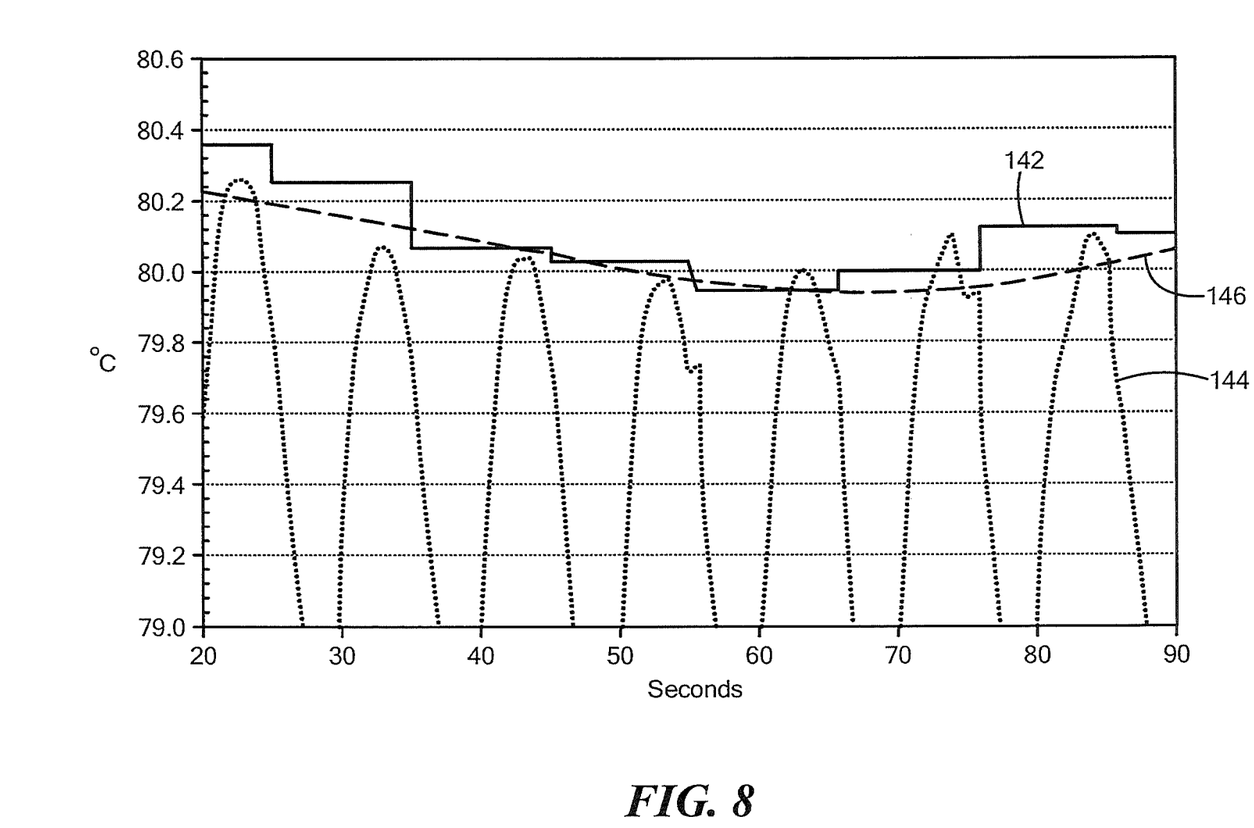
FIG. 8 is a graph further illustrating the method of the present invention.

The best estimate of slide surface temperature is extracted from the raw sensor data by capturing the most recent peak sensor temperature and reporting that temperature as feedback to the temperature control system. This data extraction is accomplished using a two-step peak detect and hold process, synchronized with the rocking mechanism: A peak detector which has been previously reset to zero tracks the sensor signal until it reaches a maximum value which it holds. After the peak is past and the chamber tilts back to a level orientation, the recent peak temperature replaces the previous peak temperature as the value used for feedback to the temperature control system 16. This process is illustrated in FIG. 8, which shows the feedback signal generated by the peak-detect and hold calculation as a solid line 142, the raw output of the temperature sensor as a dotted line 144, and the average temperature of the slide surface as a dashed line 146. FIGS. 7 and 8 show that the signal processing method produces a more accurate estimate of true slide surface temperature than would be found using the time average of the sensor signal.

The temperature sensor 60, the thermal element 50, and the agitation control system 18 are in communication with the system controller 20. The system controller receives synchronizing data from the agitation system 18 and temperature data from the temperature sensor 60, processes the data as described above, and transmits control signals to the thermal element 50 to control the heat transfer to the biological specimen.

The temperature control system 16, fluidics system 14, and agitation system 18 can be standardized between sample processing modules. Standardization of systems and components provides interchangeability of the module with a module having a housing configured to accommodate a different pre-identified sample process in a sample processing system. The temperature control system can include thermal elements that can function dependently to control temperature uniformly across all of the sample modules, or that can function independently to control temperature differently for different sample modules. The agitation system can include a single rocker table configured such that multiple sample processing modules can be agitated concurrently. In another aspect, a separate rocker table can be utilized for each module to allow non-concurrent agitation. Thus laboratory protocols can be run simultaneously that have different agitation steps, or that are spaced in time such that concurrent agitation is not desirable. Also, one sample processing module can be held in a substantially flat position while being filled, or in a tilted position toward the side of the internal space containing the fluid input. Similarly, a separate sample processing module can be held in a substantially flat position while being drained, or in a tilted position toward the side of the internal space containing the fluid output. These actions could be performed simultaneously and sequentially on multiple sample processing units. It is also contemplated that a module housing can have multiple chambers, where each chamber can process multiple sample process inserts simultaneously.

It should also be noted that in some aspects multiple sample processing modules can be concurrently utilized in the system. Furthermore, in some aspects, multiple sample processing modules that are concurrently used can have a different pre-identified sample process. In these cases, the system can be modular in nature, allowing sample processing modules with standardized temperature control, agitation, and fluidics systems to be used. Such configurations add substantially to the versatility of the system as a whole.

It is contemplated that numerous sample processes can be performed using the modules according to aspects of the present invention, and any sample process that can be performed in a module is considered to be within the present scope. A sample process can be a laboratory protocol, or a portion of a laboratory protocol. In other words, in one aspect, a sample process can encompass all of or substantially all of a laboratory protocol. As such, a sample can be introduced into a module, and a laboratory protocol can be performed thereon from start to finished product. In another aspect, a sample process can encompass a portion of a laboratory protocol. For example, a sample process can be merely a series of wash and reaction steps that are only a part of a laboratory protocol, the rest of which is performed outside of a sample module. In another aspect, a sample process that is a first portion of a laboratory protocol can be performed in one sample module, and a different sample process that is a second portion of the laboratory protocol can be performed in a different sample module. Non-limiting examples of sample processes can include in situ hybridizations such as fluorescent in situ hybridization (FISH) and whole mount in situ hybridization (WISH), blots such as Western blots, Northern blots, Southern blots, slide processing, immunohisto chemistry reactions, histopathology reactions, antibody assays, gel electrophoresis, restriction analysis, ligation, labeling, filter-based assays, and the like, including combinations thereof. In one specific aspect, the sample process can be a FISH process. In another specific aspect, the sample process can be a WISH process.

The above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein. It will also be apparent that various described features and aspects of the present invention can be arranged and rearranged in various combinations. Thus, for example, features described in association with one embodiment can be used in other embodiments.

Thus, the invention is not to be limited by what has been particularly shown and described, except as indicated by the appended claims.

What is claimed is:

1. A temperature control device comprising:
   a housing, a well within the housing configured to receive an object, at least one fluid port in the housing configured to provide fluid access to the well;
   a thermal element in heat exchange communication with fluid in the well;
   a temperature sensor disposed in the well at a location to be covered and uncovered by fluid in the well as the housing portion moves;
   an agitation system coupled to at least a portion of the housing to cause fluid flow within the well to periodically cover and uuncover the temperature sensor with fluid within the well; and
   a controller in communication with the thermal element, the temperature sensor, and the agitation system and operative to control the thermal element in correlation with temperature readings from the temperature sensor and movement of the agitation system, wherein temperature readings when the temperature sensor is covered with the fluid correspond to peak temperatures in the temperature data.

2. The device of claim 1, wherein the thermal element comprises a surface of the housing forming a portion of the well.

3. The device of claim 1, wherein the thermal element is thermally coupled to a surface of the housing.

4. The device of claim 1, wherein the thermal element is thermally coupled to a floor of the well.

5. The device of claim 1, wherein the thermal element comprises a Peltier device thermally coupled to a surface of the housing.

6. The device of claim 1, wherein the thermal element comprises a Peltier device, an etched foil heater, a wire-wound heater, a thick film heater, or a thin film heater.

7. The device of claim 1, wherein the thermal element comprises a thermally conductive wall of the housing.

8. The device of claim 1, wherein the temperature sensor comprises a probe extending through an aperture in a floor of the well.

9. The device of claim 1, wherein the temperature sensor comprises a thermistor, a resistance temperature device, or a thermocouple.

10. The device of claim 1, wherein the controller is operative to receive temperature data from the temperature sensor, to determine the peak temperatures, and to control the thermal element to provide a temperature output corresponding to a most recent peak temperature.

11. The device of claim 10, wherein the controller is further operative to control the agitation system to cause a periodic rocking of the fluid within the well.

12. The device of claim 1, further comprising a device for holding the object in the well for movement with respect to the housing.

13. The device of claim 12, wherein the holding device includes pivot pins located at a midpoint of the holding device and configured to fit within complementary recesses in opposed side walls of the well of the housing, the pivot pins configured to allow pivoting motion of the holding device with respect to the housing.

14. The device of claim 1, further comprising a plurality of wells within the housing, each well configured to receive an object.

15. An analytical system for performing laboratory protocols on an object comprising a biological specimen, comprising:
the temperature control device of claim 1; and
a fluidics system comprising an input fluid controller configured to deliver fluid to the well and an output fluid controller configured to withdraw fluid from the well.

16. The analytical system of claim 15, wherein the input fluid controller is in fluid communication with the at least one fluid port.

17. The analytical system of claim 15, wherein the output fluid controller is in fluid communication with the at least one fluid port.

18. The analytical system of claim 15, wherein the controller is in communication with the fluidics system.

19. A temperature control device comprising:
a housing, a well within the housing configured to recieve an object, at least one fluid port in the housing configured to provide fluid access to the well;
a device for holding the object in the well for movement with respect to the housing, wherein the holding device comprises a slide holder comprising a frame defining a substantially open bottom region, the frame including lips configured to support ends of a microscope slide, wherein the object comprises a biological specimen on the slide accessible to fluid within the well through the open bottom region of the frame;
a thermal element in heat exchange communication with fluid in the well;
a temperature sensor disposed in the well at a location to be covered and uncovered by fluid in the well as the housing portion moves;
an agitation system coupled to at least a portion of the housing to cause fluid flow within the well; and
a controller in communication with the thermal element, the temperature sensor, and the agitation system and operative to control the thermal element in correlation with temperature readings from the temperature sensor and movement of the agitation system.

20. A method for controlling temperature in an analytical system for performing laboratory protocols, comprising:
providing the temperature control device of claim 1;
placing a biological specimen into the well;
introducing a fluid into the well in contact with the biological specimen;
rocking the housing to cause flow of the fluid within the well to periodically cover and uncover the temperature sensor with fluid;
sensing the temperature of the fluid within the well at the temperature sensor; and
controlling the thermal element in correlation with temperature data from the temperature sensor.

21. The method of claim 20, wherein the thermal element is controlled to provide a temperature output corresponding to a most recent peak temperature in the temperature data.

22. The method of claim 20, wherein the thermal element is controlled to provide a temperature output corresponding to a time when the temperature sensor is covered with fluid.

23. A method for controlling temperature in an analytical system for performing laboratory protocols, comprising:
providing a housing having a well for containing a biological specimen;
placing the biological specimen into the well;
introducing a fluid into the well in contact with the biological specimen;
heating the fluid in the well in accordance with a predetermined protocol;
rocking the housing to cause flow of the fluid within the well to periodically cover and uncover a temperature sensor with fluid within the well;
sensing the temperature of the fluid within the chamber at a location remote from the biological specimen, wherein sensed temperatures when the temperature sensor is covered with the fluid correspond to peak temperatures in the temperature data; and
controlling the heating of the biological specimen in the chamber in correlation with temperature data from the remote location.

24. The method of claim 23, further comprising controlling the heating to provide a temperature output to the fluid corresponding to a most recent peak temperature in the temperature data.

25. The method of claim 23, further comprising controlling the heating to provide a temperature output to the fluid corresponding to a time when the temperature sensor is covered with fluid in the well.

* * * * *